United States Patent [19]
Gergely et al.

[11] Patent Number: 4,737,366
[45] Date of Patent: Apr. 12, 1988

[54] CHEWING GUM AND PRODUCTION METHOD THEREOF

[76] Inventors: Gerhard Gergely; Thomas Gergely; Irmgard Gergely, all of Gartengasse 8, A-1050 Vienna, Austria

[21] Appl. No.: 913,662
[22] PCT Filed: Dec. 21, 1985
[86] PCT No.: PCT/EP85/00735
 § 371 Date: Aug. 26, 1986
 § 102(e) Date: Aug. 26, 1986
[87] PCT Pub. No.: WO86/03967
 PCT Pub. Date: Jul. 17, 1986

[30] Foreign Application Priority Data
Dec. 27, 1984 [CH] Switzerland .......................... 6187/84

[51] Int. Cl.$^4$ .............................................. A23G 3/30
[52] U.S. Cl. ................................................ 426/5; 426/4
[58] Field of Search ...................................... 426/3-6; 424/48

[56] References Cited
U.S. PATENT DOCUMENTS

| | | | |
|---|---|---|---|
| 2,290,120 | 7/1942 | Thomas | 426/3 |
| 4,000,321 | 12/1976 | Mochizuki et al. | 426/5 |
| 4,139,589 | 2/1979 | Beringer et al. | 426/5 |
| 4,370,350 | 1/1983 | Fisher et al. | 426/5 |
| 4,405,647 | 9/1983 | Fisher et al. | 426/5 |
| 4,491,596 | 1/1985 | Elias | 426/5 |

FOREIGN PATENT DOCUMENTS

| | | |
|---|---|---|
| 350728 | 6/1979 | Austria . |
| 0151344 | 8/1985 | European Pat. Off. . |
| 2808160 | 8/1979 | Fed. Rep. of Germany . |
| 2530421 | 1/1984 | France ............................ 426/5 |
| 74297 | 8/1977 | Luxembourg . |

Primary Examiner—Jeanette Hunter
Attorney, Agent, or Firm—Marmorek, Guttman & Rubenstein

[57] ABSTRACT

A chewing gum which consists of a chewing gum base, fats or waxes, fillers, additives and active substances, the chewing gum base being present in a particle size of 0.2 to 1 mm, together with the fillers, additives and active substances, in the matrix of fats and waxes. The tablet form is preferably coated with a tablet coating. Production is effected by separately comminuting the chewing gum base on the one hand and the matrix on the other hand at low temperatures, mixing the two types of granules and then pressing the mixture on a cooled tableting press. Finally, the tablets are coated with a covering layer and slowly heated to 40°-45° C.

13 Claims, No Drawings

CHEWING GUM AND PRODUCTION METHOD THEREOF

The invention relates to a chewing gum consisting of a granulated chewing gum base and fillers, additives and active substances; it furthermore relates to a process for the production of this chewing gum, in which the chewing gum base is cooled below 0° C. and comminuted.

The chewing gum mentioned at the outset has often been proposed (DE-A No. 2808160, U.S. Pat. No. 2,290,120 and LU-A No. 74,297). All these known proposals have not been adopted in practice since combination of the individual chewing gum granules to form a cohesive mass during chewing is very poor. On the contrary, mixing the granules with sugar and other solids actually causes separation of the granules, which can be combined in the mouth by intensive compression with the tongue, only after sugar and other solids have been dissolved away.

However, a desirable chewing gum is one which immediately gives a cohesive mass, from which the sugar, flavorings and/or active substances, etc. are then slowly dissolved away, which is particularly important for bitter substances, such as, for example, certain pharmaceutical active substances. Such a chewing gum is obtained, according to the invention, by the measures of claims 1 to 3. By embedding the chewing gum granules in a matrix of fats and/or waxes, a cohesive mass is formed immediately or at least very rapidly during chewing, particularly when the matrix has diffused into the chewing gum granules and has already "plasticized" their surface.

The chewing gum-containing tablets according to the invention are also easier to handle and produce and have a longer shelf life when they are coated with a tablet coating which is known per se.

It is the further object of the invention to provide a process for the production of chewing gum, in particular pharmaceutical chewing gum, which permits the production of small product batches too and in which the active substances to be added to the chewing gum can be exactly metered. The production of pharmaceutical chewing gums on conventional chewing gum machines is in fact difficult for two reasons: first, the production volume is too large and, secondly, it is difficult to meter the active substance or to achieve uniform production of the chewing gum in the pharmaceutical sense. Moreover, the GMP (Good Manufacturing Practice) requirements are difficult to meet.

Surprisingly, however, the chewing gum according to the invention can be produced successfully by means of the measures stated in claims 4 to 7. In the process, (a) a chewing gum base is cooled to a temperature below −20° C. and comminuted to a particle size of 0.2 to 1 mm, (b) a material consisting of fats or waxes and having a melting point of 35° to 50° C. is melted, a filler is suspended in the resulting melt, and the melt is allowed to cool and is milled at a temperature below 0° C. to a particle size of 0.2 to 0.5 mm, (c) the granular chewing gum base obtained under (a) is combined with the granular material obtained under (b) in a vacuum mixing vessel by mixing at temperatures of no higher than +5° C., and an active substance, coated with a matrix or with the stated fat or wax material, and conventional additives are added, (d) the mixture thus obtained, which is kept at a temperature of no higher than +5° C., is pressed in a tableting press, preferably a cooled tableting press, to give standard pharmaceutical tablets, and the latter are stored at 10° to no higher than 20° C., and (e) the tablet-shaped chewing gum cores are coated with a top layer, then heated slowly to 35°–60° C., preferably 40°–45° C., and finally allowed to cool to room temperature.

This procedure is preferred, although it is also possible for the tablets obtained by pressing the various granules to be subjected to the heat treatment in metal sheets provided with appropriate recesses and a release coating.

In the process according to the invention, the chewing gum components are present as normal granules, which however have to be processed at temperatures of about 0° C. To prepare these granules, in stage (a) the chewing gum, which is usually supplied in sheets as a pre-prepared gum base, is brought to −20° C. and comminuted to the stated particle size of 0.2 to 1 mm on high-speed mills in conditioned rooms.

In stage (b), the material consisting of fats and/or waxes can be melted on a water bath provided with a stirrer. Conventional fillers, such as, for example, Aerosil, sorbitol, dextrin, etc., are suspended in the melt, these fillers helping to produce a millable mixture after the material has been cooled to below +5° C., preferably below 0° C., and the said mixture is comminuted to the stated particle size of 0.2 to 0.5 mm.

Examples of fats and/or waxes which can be used for this material are mono-, di- and triglycerides of saturated fatty acids containing an even number of carbon atoms and having a chain length of 10 to 18 carbon atoms, all kinds of vegetable fats, white wax (bee's wax), hardened (hydrogenated) castor oil, polyethylene glycol, polypropylene glycol, butylglycol ether, etc.

The granules obtained in stages (a) and (b) are still kept at a temperature of not more than +5° C., preferably about 0° C., introduced into a vacuum mixing vessel and combined in this by mixing at the stated temperature to give compound granules consisting of the two individual granules. This combination to give new individual granules comes about because the friction between the granular particles produces localized heating which results in fusion of the fat, so that the two types of granules become joined together.

If the two types of granules of stages (a) and (b) are not prepared simultaneously and instead granules (a) are prepared first and granules (b) are only prepared subsequently, it is advantageous to store granules (a) immediately in a tightly closing container cooled to below +5° C., until granules (b) have been prepared. Granules (a) are preferably introduced immediately into the vacuum mixing vessel cooled to below +5° C., in particular to 0° C. The vessel is then evacuated in order to exclude the effects of moisture.

In stage (c), the active substance is added, for example in acetylsalicylic acid phase coated with the above-mentioned fat or an antihistamine embedded in a matrix. This phase is combined with the gum in a manner similar to that described in connection with the granules of process steps (a) and (b). Additives, such as sugar, etc., and flavorings are then added, and the product is finally discharged from the vacuum vessel at below +5° C., preferably 0° C., through a sieve into stock containers, which are likewise kept at the stated low temperatures.

The mixture obtained is then pressed in stage (d), in a tableting press whose dies are cooled, to give standard pharmaceutical tablets.

Because the solid particles are suspended in the fats and/or waxes, the latter have somewhat thixotropic properties. The compressive pressure results in a rise in temperature; the fat or wax melts for a short time; some of it is pressed out as a result of the pressing process and simultaneously acts as a release agent with respect to the die; otherwise, it is better distributed everywhere and also fills all cavities present.

The finished tablets must immediately be stored again in a closed container; furthermore, the room must be conditioned so that atmospheric moisture cannot condense owing to the low temperature at the press.

The cores thus obtained are brittle and completely identical to pharmaceutical tablets. They become chewing gum only in stage (e), when the cores are warmed slowly, for example in the course of 10 to 20 minutes, to a temperature of 40° to 45° C., preferably during and after coating. At this temperature the fat melts, the chewing gum becomes soft, and the fats penetrate, at least superficially, into the chewing gum material, combine with this and in this way give the chewable chewing gum. The material is then cooled. Although the chewing gum granules as a whole have not yet become soft, they have softened superficially and consequently combine to form a cohesive mass in the course of a few seconds, during chewing.

A vacuum mixing container which is particularly useful for the purposes of the invention is described in AT-A No. 329013 and AT-A No.376147.

The invention is described in detail by the Examples which follow, without being restricted to these. Unless stated otherwise, all parts and percentages are based on weight.

EXAMPLE 1

100 parts of commercial chewing gum base which consist of latex and commercial additives and are supplied in the form of sheets are cooled to $-10°$ C., broken up, milled to a particle size of 0.4–0.8 mm in a cooled mill, and stored in tightly closed polyethylene containers at 0° C.

30 parts of fatty acid triglyceride are melted together with 2 parts of magnesium stearate, 4 parts of talc and 2 parts of dextrin over a water bath; during this procedure, the solids go into suspension. The material is cooled to 0° C., milled to a particle size of 0.2 to 0.5 mm in a cooled mill and likewise stored at 0° C.

The granulated gum base and fat base are introduced into a vacuum mixing vessel cooled to 5° C. with cooling brine, and solid flavorings, sweeteners and, for example, 6 parts of a coated antihistamine, such as, for example, Dramamine (Dramamine is an international abbreviated name) are added.

The vessel is evacuated in order to eliminate the effect of moist air and the danger of this condensing, and the material is mixed thoroughly by lifting and rotating the vacuum mixing kettle.

Air which has a relative humidity no higher than 10% is then allowed to flow in, and the prepared mixture is discharged through a rotating sieve into stock containers, which are likewise stored at $-5°$ to 0° C.

Pressing of the material is carried out in cooled tableting presses.

The cores can be coated either by a conventional method in which sugar solution is poured on, or by a spray method.

To carry out this procedure, the cold tablet cores are introduced into a cold coating kettle and immediately covered with sugar solution or suspension; care must be taken to ensure that an extremely small amount of material is used for the first coatings, since these initially penetrate only into the surface of the cores. However, this strengthens the core surface to a sufficient extent, so that the further procedure can be carried out with warming of the cores. Thus, a temperature of 40° to 45° C. is slowly reached in the course of 10 to 20 minutes, during application of the further layers. At this point, a coat corresponding to about 20% of the core weight should already have been applied and dried, so that, as a result of the diffusion process, i.e. through softening of the chewing gum inside, the external shell is sufficiently stable to preserve the tablet shape produced by pressing. The further tablet coats may also be applied in a conventional manner at up to 50° C., since the tablet core shows no tendency to expand or shrink and accordingly cannot cause any deformation of the tablet coat produced.

EXAMPLE 2

20 parts of hardened castor oil are melted over a water bath at 70° C. A mixture of 1 part of stearic acid, 4 parts of talc and 7 parts of dextrin is suspended therein. The suspension is allowed to cool and once again milled to a particle size of 0.2–0.5 mm in cooled mills.

In addition, 10 parts of hardened castor oil which has been melted at 60° C. are poured over 15 parts of acetylsalicylic acid, and the acetylsalicylic acid crystals are coated by rapid stirring in a planetary mixer. The acetylsalicylic acid phase prepared in this manner is introduced into a vacuum mixing kettle, together with 100 parts of chewing gum base milled as described in Example 1 and the 20 parts of the castor oil phase prepared as described above. The material is then provided with conventional additives, such as, for example, sugar, xylitol, sorbitol, flavorings, etc., and mixed at 0° C. by raising and lowering the vacuum mixing kettle.

Before the mixing process, the kettle is evacuated and dried air having a maximum relative humidity of 10% is then blown in.

Mixing in the absence of air is advantageous because the particles can come into closer contact with one another and better friction between the particles also results. Moreover, evacuation removes any superficial traces of residual moisture from the preceding processes.

Coating is also carried out as described under Example 1.

We claim:

1. A chewing gum comprising a chewing gum base in the form of particles embedded in a matrix; said particles having a size in the range of 0.2 to 1 mm; said matrix being selected from the group consisting of fats, waxes, and mixtures thereof and said matrix being 20 to 40 parts based on 100 parts of said chewing gum base.

2. The chewing gum as claimed in claim 1, further comprising at lease one filler.

3. The chewing gum as claimed in claim 1, further comprising at least one additive.

4. The chewing gum as claimed in claim 1, wherein said matrix has diffused at least partially into the surface of said particles.

5. The chewing gum as claimed in claim 1, wherein said chewing gum is physically shaped like a tablet and further comprising a tablet coating on said tablet.

6. A chewing gum as claimed in claim 1, further comprising at least one active substance.

7. A process for producing a chewing gum, comprising milling a substance at a temperature less than 0° C. to produce particles having a size in the range from 0.2 to 0.5 mm; said substance having a melting point in the range of from 35° C. to 50° C. and selected from the group consisting of fats, waxes, and mixtures thereof;
providing a chewing gum base in the form of particles having a size in the range of from 0.2 to 1 mm; and
combining the particles of said substance and the particles of said chewing gum base to produce at least one tablet in which the particles of said chewing gum base are embedded in said substance so that said substance is a matrix.

8. The process as claimed in claim 7, wherein the particles of said substance and the particles of said chewing gum base are combined so that said substance is in the range of from 20 to 40 parts based on a 100 parts of said chewing gum base.

9. The process as claimed in claim 7, wherein said combining step includes mixing the particles of said substance and the particles of said chewing gum base together in a vacuum, or at a temperature less than 5° C., or in a vacuum and at a temperature less than 5° C.

10. The process as claimed in claim 7, wherein said combining step includes combining the particles of said substance and the particles of said chewing gum base at a temperature of less than 5° C., or in a cooled tableting press, or at a temperature less than 5° C. and in a cooled tableting press.

11. The process as claimed in claim 7, further comprising coating said tablet.

12. The process as claimed in claim 11, wherein said coating step is carried out at a temperature from 35° C. to 60° C. over a period of time from about 10 to 20 minutes; and thereafter cooling said coated tablet.

13. The process as claimed in claim 12, wherein said coating step is carried out at a temperature from 40° C. to 45° C.

* * * * *